United States Patent [19]

Djananov et al.

[11] Patent Number: 6,159,476
[45] Date of Patent: Dec. 12, 2000

[54] HERBAL SUPPLEMENT FOR INCREASED MUSCLE STRENGTH AND ENDURANCE FOR ATHLETES

[75] Inventors: Atanas Russinov Djananov, Los Angeles; Tricia Grose, Sonoma, both of Calif.

[73] Assignee: Herbaceuticals, Napa, Calif.

[21] Appl. No.: 09/481,119

[22] Filed: Jan. 10, 2000

Related U.S. Application Data

[60] Provisional application No. 60/115,366, Jan. 11, 1999.
[51] Int. Cl.⁷ .................... A61K 39/385; A61K 31/14; A61K 31/44; A61K 31/12; A61K 31/525
[52] U.S. Cl. ................ 424/195.1; 514/642; 514/345; 514/251; 514/52; 514/690
[58] Field of Search ............... 424/195.1; 514/642, 514/345, 251, 52, 690

[56] References Cited

U.S. PATENT DOCUMENTS

| | | | |
|---|---|---|---|
| 5,177,070 | 1/1993 | Katz | 514/215 |
| 5,312,817 | 5/1994 | Snorrason | 514/141 |
| 5,777,108 | 7/1998 | Kosley, Jr. et al. | 540/546 |
| 5,877,172 | 3/1999 | Hille et al. | 514/215 |
| 5,958,903 | 9/1999 | Renko et al. | 514/80 |
| 5,965,571 | 10/1999 | Hutchinson | 514/297 |

*Primary Examiner*—Jerome D. Goldberg
*Assistant Examiner*—Jennifer Kim
*Attorney, Agent, or Firm*—Darby & Darby

[57] ABSTRACT

Athletic performance may be improved by administering a composition comprising galanthamine as an active ingredient to an athlete before and during sports activities. Also provided is an herbal sports performance composition comprising whole plant extract of *Leucojum aestivum*.

1 Claim, No Drawings

HERBAL SUPPLEMENT FOR INCREASED MUSCLE STRENGTH AND ENDURANCE FOR ATHLETES

This patent application claims the priority of U.S. provisional patent application Ser. No. 60/115,366, filed Jan. 11, 1999 which is incorporated herein by reference.

FIELD OF THE INVENTION

The present invention relates to a method of enhancing muscle strength and endurance in an athlete by administering a dietary supplement comprising an herbal extract or preparation containing galanthamine.

BACKGROUND OF THE INVENTION

Motive nerve impulses are transmitted as electrical signals along a motorneuron until they reach the neuron ending located on a muscle. The nerve ending contains vesicles filled with acetylcholine, which is the main neurotransmitter in the human body. The nerve impulse stimulates the vesicles to release acetylcholine into the synapse through the pores in the pre-synapse membrane. The acetylcholine diffuses through the synapse gap very quickly (within 1 millisecond) and reaches the post-synapse membrane. The acetylcholine depolarizes the post-synapse membrane, generating an electrical impulse which spreads along the muscle fiber and causes the muscle to contract. This system of neuron-synapse-muscle operates as an "all-or-none" response, that is the stimulus must overcome an excitatory threshold in order for the signal to be transmitted and the muscle to contract. The thresholds of excitation are different for different muscle motor units. A motor unit is defined as the system of one motor nerve, its branches, the synapses located at the end of the branches, and the muscle fibers that are stimulated by the nerve. Both the threshold of excitation and the strength of the incoming nerve impulses can vary to a great degree. An increase in stimulus intensity may bring progressively more units to respond. In fact, improvement in strength, speed and endurance depend mainly on the body's ability to mobilize a greater number of muscle fibers in the contraction. This ability is greatly influenced by temporary factors such as fatigue, stress level and food intake, and by long-term factors such as genetics, general fitness level, conditioning, hormonal levels, age, etc. In the average non-training individual, only about 20–30% of the available muscle fibers become actively involved in the muscle contraction. This percentage is raised in professional athletes to about 40–50% by regular and intensive workouts. Regular workouts, good nutrition and appropriate supplementation lead to an increase in the energy levels of the muscle cell, as well as to an extended growth and branching out of the capillary network, and the optimization of the work of numerous enzyme systems, etc., the result of all this being the lowering of the excitation threshold of the muscle fibers, which facilitates muscle contraction.

The passage of the impulses through the synapse is brief and unidirectional. Once acetylcholine has conveyed the nerve impulses across the synapse, it must be cleared from the gap. The body does this by breaking it down, or hydrolyzing it, to choline and acetyl, using acetylcholinesterase, or simply cholinesterase. Cholinesterase however eliminates some acetylcholine that has not reached the post-synapse membrane, therefore an 100% effective transmission of the nerve impulse through the synapse does not occur. In addition, after continuous or repetitive movement or exercise, fatigue reduces the strength and duration of the impulses generated, and stimulates the release of the inhibitory neurotransmitter gamma aminobutyric acid, which overpolarizes the post-synapse membrane. The amount of acetylcholine released by the pre-synapse membrane also decreases. As a result of these factors, the energy level of the muscle cell is decreased and the excitation threshold becomes more difficult to overcome.

Galanthamine is a known acetylcholinesterase inhibitor. Galanthamine reversibly binds to acetylcholinesterase, inhibiting its action and resulting in an increase in local concentrations of acetylcholine. Galanthamine has been used in the treatment of different diseases of the nervous system such as Alzheimer's disease (U.S. Pat. No. 5,958,903) and Parkinson's disease (U.S. Pat. No. 5,965,571); the treatment of chronic fatigue syndrome (U.S. Pat. No. 5,312,817); as an erectogenic agent in the treatment of male sexual dysfunction (U.S. Pat. No. 5,177,070) as well as the treatment of glaucoma, myasthenia gravis and senile dementia.

Galanthamine is typically used in pharmaceutical compositions in purified form and is obtained by complex chemical extractions from plant sources (U.S. Pat. No. 5,877,172) or chemically synthesized (U.S. Pat. Nos. 5,777,108 and 5,958,903). These processes may be disadvantageous in that they utilize undesirable chemicals such as chlorohydrocarbons and purification processes forming galanthamine salts.

There is great interest in improving the strength, speed and endurance of physical performance, particularly in athletes. One factor which enables athletes to achieve high level performance in sports, particularly in strength and power events, such as weightlifting and body building, is to increase muscular quality, that is to increase the effectiveness of muscle fiber contraction. An inexpensive, non-toxic preparation, preferably in an herbal formulation containing a whole plant extract that enhances the performance of muscle contraction in individuals, thereby improving physical performance, has heretofore not been disclosed.

SUMMARY OF THE INVENTION

The present invention provides a method for enhancing the sports performance of an athlete by administering to an athlete a composition comprising galanthamine as an active ingredient. The galanthamine is administered in an amount effective to increase the strength, endurance and speed of muscle contraction, thereby improving the quality of an athlete's sport performance. The galanthamine is preferably provided as a component of a dried whole plant or plant extract, most preferably *Leucojum aestivum*.

The applicants have found that a daily dose of from about 2–15 mg of galanthamine unexpectedly improves the effectiveness of muscle performance, allowing athletes to achieve a high level performance in sports, particularly in strength and power events, such as weightlifting and body building, by increasing muscular quality, that is increasing the effectiveness of muscle fiber contraction.

The present invention also provides a novel herbal composition comprising galanthamine as at least one active ingredient present in a powdered form of a whole plant extract that provides strength, endurance and speed in sport performance. In one embodiment, the composition also comprises a combination of naturally occurring substances such as B vitamins, Co-Q10, green tea and Ganoderma extracts, nonessential amino acids, antioxidants and minerals which in combination with the whole plant extract enhance the effectiveness of muscle performance. In a preferred embodiment the whole plant extract is of the plant

*Leucojum aestivum.* The whole plant extract is present in the herbal composition in an amount of from 0.1–3 wt %.

DETAILED DESCRIPTION OF THE INVENTION

The present invention concerns novel dietary compositions, a method for their preparation, and a method of using the compositions for improvement of sports performance. At least one of the active ingredients in the composition is most notably a cholinesterase inhibitor.

The term "sports performance" as used herein, refers to the ability of the athlete's muscles to perform when participating in sports activities. Enhanced sports performance, strength, speed and endurance are measured by an increase in muscular contraction strength, increase in amplitude of muscle contraction, shortening of muscle reaction time between stimulation and contraction.

The term "athlete" refers to an individual who participates in sports at any level and who seeks to achieve an improved level of strength, speed and endurance in their performance. The present invention is particularly beneficial to those athletes who are body builders. However, those athletes who are bicyclists, long distance runners, short distance runners will also benefit from the effects of the present invention. An athlete may be hard training, that is, performs sports activities intensely more than three days a week or for competition. An athlete may also be a fitness enthusiast who seeks to improve general health and well-being, improve energy levels, who works out for about 1–2 hours about 3 times a week.

A method of lowering the excitation threshold of muscle fibers and maintaining the lower level for improvement of strength, endurance and speed of muscle contraction is found to be greatly beneficial to those individuals seeking to improve the quality of their sports performance. While the dietary supplement may be used by individuals who are not in athletic training, the supplement is ideal for use by athletes to improve sports performance.

Enhanced sports performance in manifested by the ability to overcome muscle fatigue, ability to maintain activity for longer periods of time, and have a more effective workout. It is believed that galanthamine improves athletic performance through its properties of increasing the strength of muscle contractions, maintaining a lower excitation threshold for a longer period of time delaying the onset of fatigue in muscles, and decreasing the latent period (reaction time) for a muscle contraction, so that the muscles can be stimulated more often and work more. This may also be beneficial to physical activity involving repetitive motion.

In one aspect, the invention provides a method of enhancing muscle performance by administering a dietary supplement comprising galanthamine. Galanthamine is an alkaloid from the family of Amaryllidaceae that can be isolated from snowdrop *Galanthus Nivalis,* or preferably *Leucojum aestivim.* Galanthamine can also be chemically synthesized using known methods (e.g., Bulgarian patent No. 25140) and may be provided as a salt, for example, in the form of galanthamine hydrobromide.

Galanthamine may be administered orally or parenterally, i.e. by injection. The optimal daily dose is from about 2 to 15 mg. It can be taken up to 6 months without a break. A typical regimen may be a daily dose administered for 50–90 days, followed by a 30–40 day cessation of administration. For sports use, it is preferred that 5–10 mg is taken 1½–2 hours before workout. On non-training days, a maintenance dose of 2.5–5 mg, which can be divided into 2 intakes, set about 12 hours apart, is preferred.

For the hard training athlete the preferred dose range is 5–7 mg daily on active days with 3–4 mgs daily dose for maintenance on days off. For fitness enthusiasts a daily dose of about 3–4 mg daily before a workout is preferred, with the same dose divided into two equal portions taken at 12 hour intervals on the off days.

Galanthamine hydrobromide may be administered for the purposes of the present invention in the form of capsules or caplets, although other conventional oral dosage forms such as tablets may also be used. In preparing capsules or tablets, standard tablet or capsule making techniques may be employed.

In another aspect of the invention, the inventors have found that the whole plant extract of *Leucojum aestivum,* in combination with the coenzyme Co-Q10 plus vitamin B and other herbal extracts, works synergistically to promote improved sports performance. It is believed that at least one of the active ingredients in the whole plant extract, galanthamine, in its capacity as an acetylcholinesterase inhibitor, increases muscle resistance to fatigue by maintaining a lower excitation threshold level for longer periods of time. The active ingredients secure stronger impulses which, when transmitted to the muscles, generate stronger muscle contractions. Each of the constituents of the combined herbal preparation of the invention has an individual tendancy to enhance physical well being. However, the combination of *Leucojum aestivum,* coenzyme Co-Q10 plus vitamin Bs (including niacin, thiamine vitamin $B_{12}$ and vitamin B complex) and other herbal extracts, when administered in proper concentration, stimulate stronger muscle fiber contractions to allow for more sustained and effective physical activity. The ingredients may further stimulate the release of acetylcholine in the neuron endings and increase the sensitivity of the post-synapse membranes.

Although one of the active ingredients, galanthamine, found in the whole plant extract of *Leucojum aestivim* can be synthesized by known methods, Applicants have found that using the whole plant extract provides beneficial results. It is believed that the additional components contained within the plant cell wall as well as the other ingredients contained in the composition as described herein provide an unexpected synergistic effect on muscle performance. An added advantage is the use of herbal based compositions providing many beneficial results. This is particularly advantageous for those individuals reluctant to use pharmaceuticals containing synthetic chemicals because of potential side effects of long term use or where no nonprescription remedy is available.

For purposes of the invention, a process for preparing the whole plant extract *Leucojum aestivim* is described as follows: the mucilage is removed from intact plants, the remaining plant material is pulverized or finely chopped in a blender, the pulverized plant material is steam distilled, and then triple washed with water. The treated plant material is then combined with the washings and the mucilage to form the whole plant extract. The whole plant extract may be used unfiltered, or may be filtered through a Whatman filter. Alternatively the resulting whole plant extract may be dried to a powder by air drying at room temperature or accelerated drying at 37° C. The whole plant extract is preferably stored in a dark container at room temperature in a moisture-free environment until used.

Additional organic ingredients may be added to activate incidental benefits. The supplement may further contain ingredients that improve oxygen metabolism, antioxidants, factors which directly or indirectly are related to radical scavengers or improve cardiac function. While any of these constituents taken alone would be insufficient to produce the desired result, in combination they work synergistically to produce significant enhancement of physical sports activity. The constituents are not toxic in the amounts provided and have no known side-effects.

The composition may thus further include a combination of naturally occurring substances such as herbs, growth factors, enzymes such as coenzyme Q10 (CoQ10) chemically known as 2,3-dimethoxy-5-methyl-6-decaprenyl-1,4-benzoquinone, a fat soluble quinone, which is an essential component of the mitochondrial respiratory chain and may be important in producing energy for all the body's activities; hormones; amino acids; trace elements, vitamins and minerals, particularly in amounts 100–500% of RDA; compounds such as antioxidants present in extracts of Chinese plants and herbs such as green tea and fungi of the genus Ganoderma and other nonessential nutrients such as N-acetyl cysteine (NAC), a non-essential amino acid, believed to benefit brain function. The composition can further include choline, a component of the neurotransmitter acetylcholine, in supplemental doses in the range of about 50–200 mg, which may increase the level of acetylcholine produced, assist in maintaining the integrity of neuronal membranes and enhance synaptic transmissions; and L-carnitine, a metabolic cofactor, which promotes neurological recovery from trauma. These ingredients in combination with the active enhance the speed, endurance and strength of muscle performance, particularly in an athlete.

For the herbal preparation, the composition of the invention comprises the ingredients provided in Table 1.

TABLE 1

| Ingredient | Broad range (wt %) | Preferred range (wt %) |
| --- | --- | --- |
| Leucojum aestivum | 0.25–4.5 | 0.3–3.5 |
| Thiamine | 0.5–4 | 1.5–3.0 |
| Inositol Hexanicotinate | 3.0–6.5 | 4.1–5.6 |
| Vitamin $B_{12}$ | 0.0001–0.001 | 0.0003–0.0006 |
| Vitamin B complex | 0.05–0.3 | 0.08–0.2 |
| Green Tea | 1.9–4.5 | 2.5–3.9 |
| Ganoderma | 0.5–4.0 | 1.5–3.0 |
| N-acetyl-L-cysteine | 50–75 | 60–70 |
| L-carnitine | 5–10 | 7.5–9.0 |
| Co-Q10 | 4.0–7.3 | 5.3–7.0 |
| calcium (as calcium pantothenate | 3.0–6.3 | 4.1–5.6 |

The desired effect is best achieved with a dose comprising the following preferred concentrations:

2.5 mg (0.5 wt %) of the whole plant extract of *Leucojum aestivum*
25 mg (5.1 wt %) Inositol Hexanicotinate
12.5 mg (2.6 wt %) Thiamine
0.012 mg (0.00045 wt %) Vitamin $B_{12}$ (equivalent to about 200% RDA)
5 mg (0.1 wt %) Vitamin B
15 mg (3.1 wt %) Green tea
12.5 mg (2.6 wt %) Ganoderma
320 mg (65.6 wt %) N-acetylcysteine (NAC)
40 mg (8.2 wt %) L-carnitine
30 mg (6.2 wt %) CO-Q10
25 mg (5.1 wt %) calcium (as calcium pantothenate).

In the case of the herbal composition of the invention, the preferred dosage form is a capsule. In this manner the free flowing powders of the herbal extracts and other components in the composition of the invention are readily absorbed into the body.

The invention can be better understood by reference to the following Example, which is provided by way of illustration and not by way of limitation.

EXAMPLE

In order to demonstrate the effect of the method of the present invention on athlete strength and endurance the following study is conducted:

30 healthy individuals, both male and female, ages 18–28, are separated into 2 groups, 15 persons each, to observe the changes in their strength and endurance after administration of galanthamine and regular physical training. All subjects are athletes who have exercised regularly in the gym for 1 to 3 years. During the 3 week test period, all subjects train about 4 times a week with a special exercise program for the first week as described below, supplemented with the subjects' own preferred training schedule. Strength and endurance were observed through 6 basic exercises involving the major muscle groups as follows:

1. Bench press—for the chest muscles
2. Lateral pull downs—for the back muscles 3. Press behind neck—for the shoulder muscles
4. Bicep curls
5. Tricep pushdowns
6. Squats—for the leg muscles 10 participants in each group take galanthamine, the other 5 take a placebo. The dosage of galanthamine is 7.5 mg daily taken with a meal 1.5–2 hours before the workout on training days and 5 mg daily on non-training days divided into two equal portions taken in the morning and in the afternoon.

2. The Strength Group.

a. The initial level. Before administration of galanthamine the initial strength level of each subject is determined and is defined as the maximum weight a subject is able to lift in all 6 exercises.

b. The training schedule. The subjects use a split training method, that is they alternate on one day training their chest, back and shoulder muscles (performing exercises #1, 2 and 3, respectively) and the next day train their biceps, triceps and legs (exercises #4, 5 and 6, respectively). The subjects do 5–6 sets in each exercise using a pyramidal principle for increasing their strength, i.e. they start every exercise doing 10–15 repetitions using a middle weight, then increase the weight gradually, being able to do fewer repetitions, until the maximum weight they are able to lift for one repetition with difficulty is reached. 2 sets are then performed using the same or 5–10% less weight. This maximum weight is considered the "record for the day", and is compared to the initial level.

c. The results. An increase in strength is observed almost immediately after administration of galanthamine. After 1 week, the average increase in strength is about 4–7%. After the initial increase, strength increases at a slower rate and by the third week, increases by a total of 10–13% The subjects taking the placebo show an approximate 1–3% increase in strength within the period of the trial, as a result of exercise alone. Athletes who continue to take galanthamine for up to 3 months report an increase in strength of over 20% during the entire period.

3. The Endurance Group.

a. The initial level. The subjects establish the initial maximum weight they are able to lift in the 6 exercises in the same manner as the strength group. The subjects perform as many repetitions as possible using these weights and the number of the maximum repetitions is considered to be the base initial endurance level. Endurance is estimated as 50% of the maximum weight able to be lifted.

b. The training schedule. Exercises 1, 2 and 3 are performed on one day and exercises #4, 5 and 6 on alternate days. The subjects use only one weight in each exercise but gradually increase the number of repetitions. The subjects perform 10 repetitions in the first set, 20 repetitions in the second set (both as a warm-up) and as many repetitions as possible in the third set. After a 1–2 minute rest, 2 more sets are performed, while the subjects try to add at least 1–2 repetitions more than the previous set. The maximum number of repetitions is compared with the initial level.

b. The results. An improvement in endurance in the subjects taking galanthamine is observed almost immediately. After the first week, the average endurance increases by 11% and by the end of the trial, after 3 weeks of treatment with galanthamine the average endurance increases by 24%. The subjects taking the placebo show only a 5% increase in endurance for the entire period.

3.Conclusion.

The administration of galanthamine for 3 weeks increases the strength and the endurance of active athletes.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims. Various patents, patent applications, and publications are cited herein, the disclosures of which are incorporated by reference in their entireties.

What is claimed is:

1. An herbal composition for improving the effectiveness of muscle performance in an athlete, comprising about 0.5 wt % of whole plant extract of *Leucojum aestivum;* about 5.1 wt % inositol hexanicotinate; about 2.6 wt % thiamine; about 0.1 wt % Vitamin Bs; about 3.1 wt % green tea; about 2.6 wt % Ganoderma; about 65.6 wt % N-acetylcysteine; about 8.2 wt % L-carnitine; about 6.2 wt % Co-Q10; and about 5.1 wt % calcium pantothenate.

* * * * *

UNITED STATES PATENT AND TRADEMARK OFFICE
CERTIFICATE OF CORRECTION

PATENT NO. : 6,159,476
DATED : December 12, 2000
INVENTOR(S) : Atanas Russinov DJANANOV and Tricia GROSE It is certified that errors appear in the above-identified patent and that said Letters Patent is hereby corrected as shown below:

Foremost page, [22], Filing date, change "Jan 10, 2000" to -- Jan 11, 2000 --.

Signed and Sealed this

Twenty-ninth Day of May, 2001

Attest:

NICHOLAS P. GODICI

*Attesting Officer*       *Acting Director of the United States Patent and Trademark Office*